United States Patent [19]

Shapiro et al.

[11] Patent Number: 5,687,738
[45] Date of Patent: Nov. 18, 1997

[54] APPARATUS AND METHODS FOR ANALYZING HEART SOUNDS

[75] Inventors: Joseph Isaac Shapiro, Aurora; Howard David Weinberger, Denver, both of Colo.

[73] Assignee: The Regents of the University of Colorado, Boulder, Colo.

[21] Appl. No.: 498,673

[22] Filed: Jul. 3, 1995

[51] Int. Cl.$^6$ .................................................. A61B 5/02
[52] U.S. Cl. ........................................... 128/715; 128/716
[58] Field of Search ................................. 128/696, 715, 128/716, 719, 700, 701, 773, 670, 671; 364/413.03, 413.06

[56] References Cited

U.S. PATENT DOCUMENTS

| | | | |
|---|---|---|---|
| 4,254,302 | 3/1981 | Walshe | 179/1 |
| 4,362,164 | 12/1982 | Little et al. | 128/639 |
| 4,528,689 | 7/1985 | Katz | 381/67 |
| 4,594,731 | 6/1986 | Lewkowicz | 381/67 |
| 4,720,866 | 1/1988 | Elias et al. | 381/67 |
| 4,765,321 | 8/1988 | Mohri | 128/715 |
| 4,792,145 | 12/1988 | Eisenberg et al. | 128/715 |
| 4,991,581 | 2/1991 | Andries | 128/715 |
| 5,002,060 | 3/1991 | Nedivi | 128/671 |
| 5,010,889 | 4/1991 | Bredesen et al. | 128/715 |
| 5,025,809 | 6/1991 | Johnson et al. | 128/715 |
| 5,086,776 | 2/1992 | Fowler, Jr. et al. | 128/715 |
| 5,213,108 | 5/1993 | Bredesen et al. | 128/715 |
| 5,218,969 | 6/1993 | Bredesen et al. | 128/710 |
| 5,301,679 | 4/1994 | Taylor | 128/773 |

FOREIGN PATENT DOCUMENTS

| | | | |
|---|---|---|---|
| 4231629 | 5/1993 | Germany | 128/715 |

OTHER PUBLICATIONS

Soliman et al., "Continuous and Discrete Signals and Systems," Prentice Hall, New Jersey, 1990, p. 348.

*Primary Examiner*—Lee S. Cohen
*Assistant Examiner*—Bryan K. Yarnell
*Attorney, Agent, or Firm*—Jennifer L. Bales

[57] ABSTRACT

Apparatus for assisting in the analysis of heart sounds monitors heart sounds, ECG, and respiratory data. Once digitized, this data is processed and analyzed to determine timing relationships between the three signals, frequency (or pitch) of sounds, and dependence or non-dependence of sounds on ECG and respiratory phase. The user of the apparatus inputs the place of detection and the maneuver being performed. Raw phonocardiogram data is displayed. The user inputs the number of beats and the frames per second to display. Fast Fourier transformed and signal averaged data are displayed, and phase sensitive and non-phase sensitive sounds are extracted. A lesion fitting algorithm suggests diagnoses and possible further maneuvers to perform. The data obtained is compared to a historical patient data.

19 Claims, 11 Drawing Sheets

HEART SOUNDS

| ASCULTATION | ABNORMALITY | LESION | CONFIRMATION |
|---|---|---|---|
| S1 | LOUD 1 | MITRAL STENOSIS | ASSOCIATED MURMUR AND OS |
|  | SOFT 1 | MITRAL REGURGITATION | ASSOCIATED MURMUR HAND GRIP |
| S2 | LOUD A2 | AORTIC REGURGITATION | ASSOCIATED MURMUR(S) HAND GRIP |
|  |  | HYPERTENSION | CLINICAL FINDINGS |
|  | SOFT A2 | AORTIC STENOSIS | ASSOCIATED MURMUR(SEM) EJECTION CLICK SUGGEST ECHOCARDIOGRAM |
| S2 | A2 P2 INTERVAL DOES NOT VARY WITH RESPIRATION | ATRIAL SEPTAL DEFECT | LOOK FOR ASSOCIATED FINDINGS WHICH SUGGEST PULMONARY HYPERTENSION |

EXTRA SOUNDS

| TIMING | FREQUENCY | LESION | CONFIRMATION |
|---|---|---|---|
| EARLY SYSTOLE CONSTANT | HIGH | AORTIC STENOSIS | ASSOCIATED MURMUR AND OS HAND GRIP/VALSALVA |
| EARLY SYSTOLE VARIABLE | HIGH | EJECTION CLICK MITRAL PROLAPSE CLICK | ASSOCIATED MURMUR(S) HAND GRIP/VALSALVA |
| EARLY DIASTOLE | HIGH | MITRAL STENOSIS | ASSOCIATED MURMUR DIASTOLIC RUMBLE |
| EARLY DIASTOLE | LOW | THIRD HEART SOUND | LOUDEST OVER APEX |
| LATE DIASTOLE | LOW | FOURTH HEART SOUND | LOUDEST OVER APEX, TIMING RELATED TO P WAVE ON ECG |

*Fig. 7A*

MURMURS

| TIMING | FREQUENCY | LESION | CONFIRMATION |
|---|---|---|---|
| SYSTOLE (STARTS AFTER S1 AND ENDS BEFORE S2) | MID-HIGH | AORTIC STENOSIS | ASSOCIATED EJECTION CLICK |
| TIMING IS FAIRLY CONSTANT | | VS PULMONIC STENOSIS VS INNOCENT FLOW MURMUR | HAND GRIP/VALSALVA LOCATION/RADIATION |
| SYSTOLE (AS ABOVE) | MID-HIGH | MITRAL PROLAPSE | VARIABLE TIMING CLOCK |
| TIMING MAY VARY | | WITH REGURGITATION | HAND GRIP/VALSALVA |
| SYSTOLE (AS ABOVE) | MID-HIGH | TRICUSPID REGURGITATION | LOUDEST AT LSB INCREASES WITH INSPIRATION |
| PAN SYSTOLIC | HIGH | MITRAL REGURGITATION | LOUDEST OVER APEX INCREASES WITH HAND GRIP |
| EARLY DIASTOLE | HIGH | AORTIC REGURGITATION | ASSOCIATED MURMURS LOCATION WHERE MURMUR IS LOUDEST |
| | | VS PULMONIC REGURGITATION | HAND GRIP/VALSALVA RESPIRATION DEPENDENCE |

*Fig. 7B*

APPARATUS AND METHODS FOR ANALYZING HEART SOUNDS

BACKGROUND OF THE INVENTION

1. Field of the Invention

This invention relates to apparatus and methods for analyzing heart sounds. More specifically, this invention relates to visual and computer assisted analysis of digitized heart sounds.

2. Description of the Related Art

The normal human heart is a four chambered structure, shown schematically in FIG. 1. It is arbitrarily divided into a right side (patient's right side) which accepts deoxygenated blood returning from the body through the venae cavae and pumps this blood into the lungs through the pulmonary artery. The lungs re-oxygenate the blood and excrete carbon dioxide. The re-oxygenated blood returns to the left side of the heart through the pulmonary veins and is pumped to the body through the aorta.

Both the right side and the left side of the heart have ventricles which actively pump blood during the contraction phase of the cardiac cycle (called systole) and atria which function to assist ventricular filling during the relaxation phase of the cardiac cycle (called diastole). On the right side of the heart, the tricuspid valve separates the right atrium and ventricle. The pulmonic valve separates the right ventricle and pulmonary artery. On the left side of the heart, the mitral valve separates the left atrium and ventricle, and the aortic valve separates the left ventricle and aorta.

Normal heart sounds are produced by the closure of the valves separating the atria from the ventricles (called the first heart sound, S1) and the subsequent closure of the valves separating the ventricles from their attached arteries (called the second heart sound, S2). The first heart sound, S1, has two components, T1 and M1. T1 is caused by the closure of the tricuspid valve. M1 is caused by closure of the mitral valve.

Similarly, the second heart sound, S2, has two components, A2 and P2. A2 is caused by closure of the aortic valve, and P2 is caused by closure of the pulmonic valve. In a normal individual, mitral valve closure (M1) precedes tricuspid valve closure (T1) slightly. Aortic valve closure (A2) normally precedes pulmonic valve closure (P2) by a varying amount, depending on the respiratory cycle. Normally, A2 precedes P2 by a longer period during inspiration than during expiration. All of these normal heart sounds are in the low frequency end of the human hearing range, falling between 30 and 250 Hz in frequency.

Abnormal heart sounds may be produced by rapid filling of dilated ventricles, producing a third heart sound called S3, as well as by the contraction of the left atrium against a non-compliant left ventricle, producing a fourth heart sound called S4. Other abnormal heart sounds and murmurs may be produced by a variety of different pathological conditions.

The timing of abnormal heart sounds, relative to other heart sounds, to respiratory cycle, and to the electrical impulses causing the heart to beat, is important in diagnosing the condition causing the abnormal sounds. FIG. 2 shows the relationship between the electrical impulse (normally detected by an ECG), the respiratory cycle, and normal heart sounds. Ventricular excitation is detected by the QRS complex of the ECG. When the ventricles are electrically excited, contraction occurs which results in increases in ventricular pressure. When the pressure in the left and right ventricles exceed that in their corresponding atria, closure of the mitral valve (M1) and tricuspid valve (T1) occur, respectively. Usually, M1 and T1 overlap, so that S1 is one continuous sound rather than being split.

When ventricular contraction ceases and relaxation of the ventricular muscle occurs, pressure decreases in the ventricle. When the pressure in the left and right ventricles falls below that of the aortic artery and pulmonic artery, respectively, aortic closure (A2) and pulmonic closure (P2) occur. The sum of A2 and P2 form the second heart sound (S2). S2 is usually split into separate, identifiable A2 and P2 sounds. The period between A2 and P2 is normally greater when the patient is inhaling rather than exhaling.

Changes in the timing relationship or intensity of these normal sounds can indicate a physical problem. The existence of extra, abnormal heart sounds also frequently indicates some physical pathology. Various clues assist the physician in determining what condition is causing the extra sound. Frequency or pitch of extra sounds, their timing and duration, and their intensity are all related to their cause. Physiologic maneuvers, such as hand grip and valsalva (expiration against a closed glottis), which alter the amount of venous return as well as left ventricular afterload, can be used to accentuate or diminish the intensity of some abnormal heart sounds and murmurs, and can, thus, be used to aid in differential diagnosis.

The relationship between abnormal heart sounds and underlying physical pathologies has long been appreciated by cardiologists. However, clinical auscultation (examination by listening to body sounds) of heart sounds is an extremely difficult skill to master. The sounds are low pitched and close together, and it is difficult for humans to separate sounds out or remember sounds accurately. Even when auscultation is performed expertly, the data derived from the examination is expressed semi-quantitatively at best in the form of a note in the patient's file. No record of the actual data is available for further analysis or comparison with data from prior or subsequent examinations.

A variety of inventions have been developed to assist physicians and other care givers with cardiac auscultation. None of these devices has been successful, due to several disadvantages discussed below. It is known in the art to provide a slowed down audio signal of a heartbeat. See, for example, U.S. Pat. No. 4,528,689 by Katz. It is also known to use an electronic stethoscope to display heart sounds visually. See U.S. Pat. Nos. 5,213,108, 5,218,969, and 5,010,889 by Bredeson et al., 5,025,809 by Johnson et al., 4,765,321 by Mohri, 4,254,302 by Walsh, 4,594,731 by Lewkowiez and 4,362,164 by Little. Some of these references discuss computer assisted diagnosis based on the heart sounds. It is also known to take frequency domain (fast Fourier transform) data of the heart sounds in order to aid in diagnosis. See, for example, U.S. Pat. Nos. 4,792,145 by Eisenberg et al., 5,301,679 by Taylor, 5,002,060 by Nedivi, and 4,720,866 Elias et al.

None of these inventions, or any other known prior art references are useful in normal diagnostic situations, because they do not provide any means of separating background noise from heart sounds. In addition, these inventions do not provide quantitative timing comparisons between heart sounds, respiratory cycle, and electric impulse.

SUMMARY OF THE INVENTION

An object of the present invention is to provide apparatus and methods to allow visual and computer assisted interpretation of heart sounds.

In order to accomplish this object, apparatus is provided for simultaneous detection of ECG signals, heart sounds and respiration. These three signals are digitally processed and displayed visually to allow the user to visually interpret heart sounds based on their timing compared to other heart sounds, to respiration and to ECG signals.

After the data is digitized, heart sound data is gated according to the QRS complex of the ECG data to synchronize the heart beats. The data associated with each heart beat is fast Fourier transformed to prevent small timing differences in heart beats from resulting in loss of data during signal averaging. Apparatus is provided to perform time averaging on a series of fast Fourier transformed (FFT) heart beat data in order to remove background noise. This signal averaged data is displayed for user interpretation.

As a feature of the present invention, the apparatus may suggest maneuvers to be performed on the patient by the operator in order to collect more data. The apparatus may also suggest diagnoses and compare the processed data to historical patient data.

Those having normal skill in the art will recognize the foregoing and other objects, features, advantages and applications of the present invention from the following more detailed description of the preferred embodiments as illustrated in the accompanying drawings.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 7, comprising FIGS. 7A and 7B is a chart showing an example of a diagnostic approach taken by the signal processor and analyzer of FIG. 3.

DETAILED DESCRIPTION OF THE PREFERRED EMBODIMENTS

Figure 1:
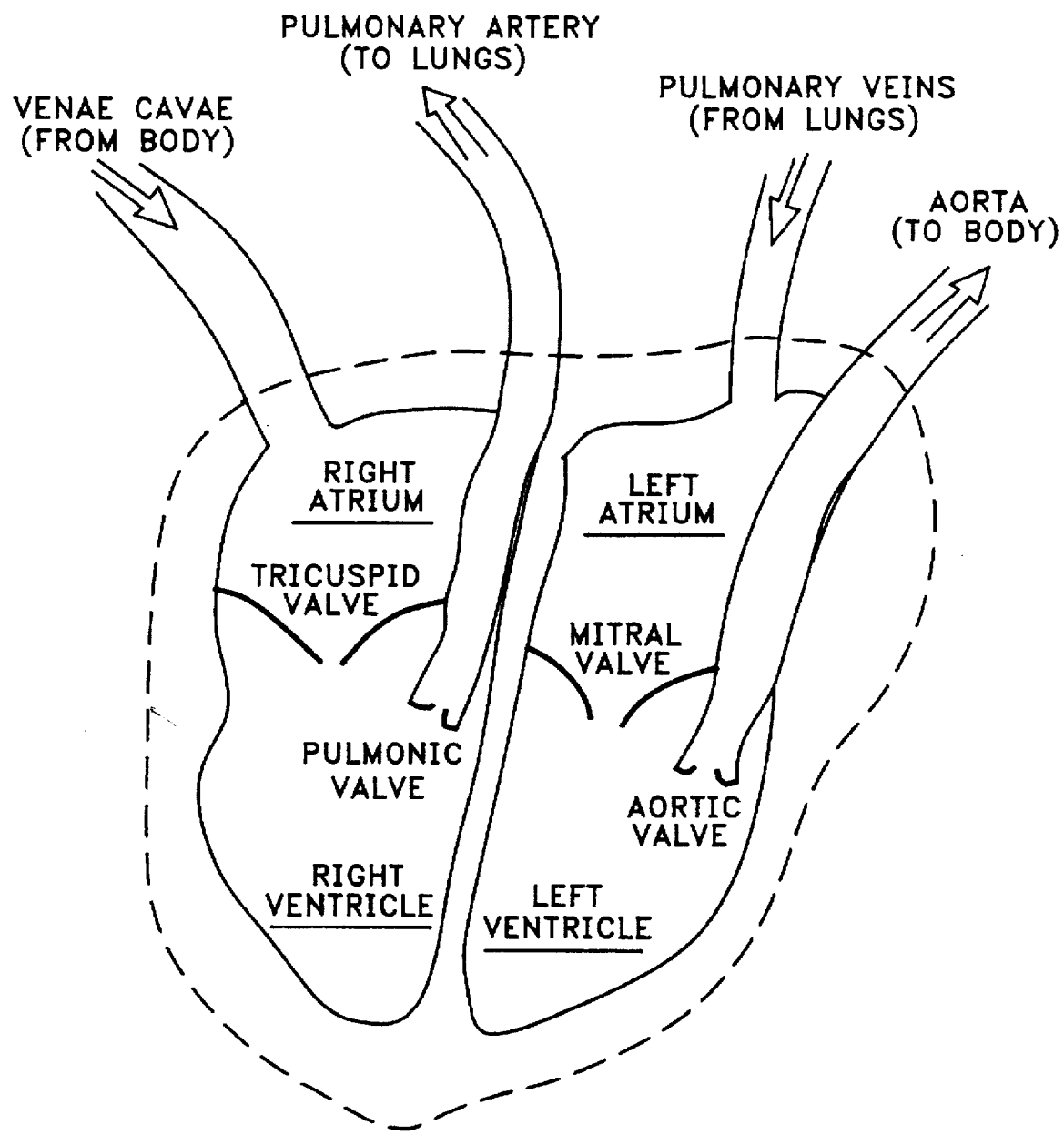
FIG. 1 is a schematic representation of a normal human heart.
Figure 2:
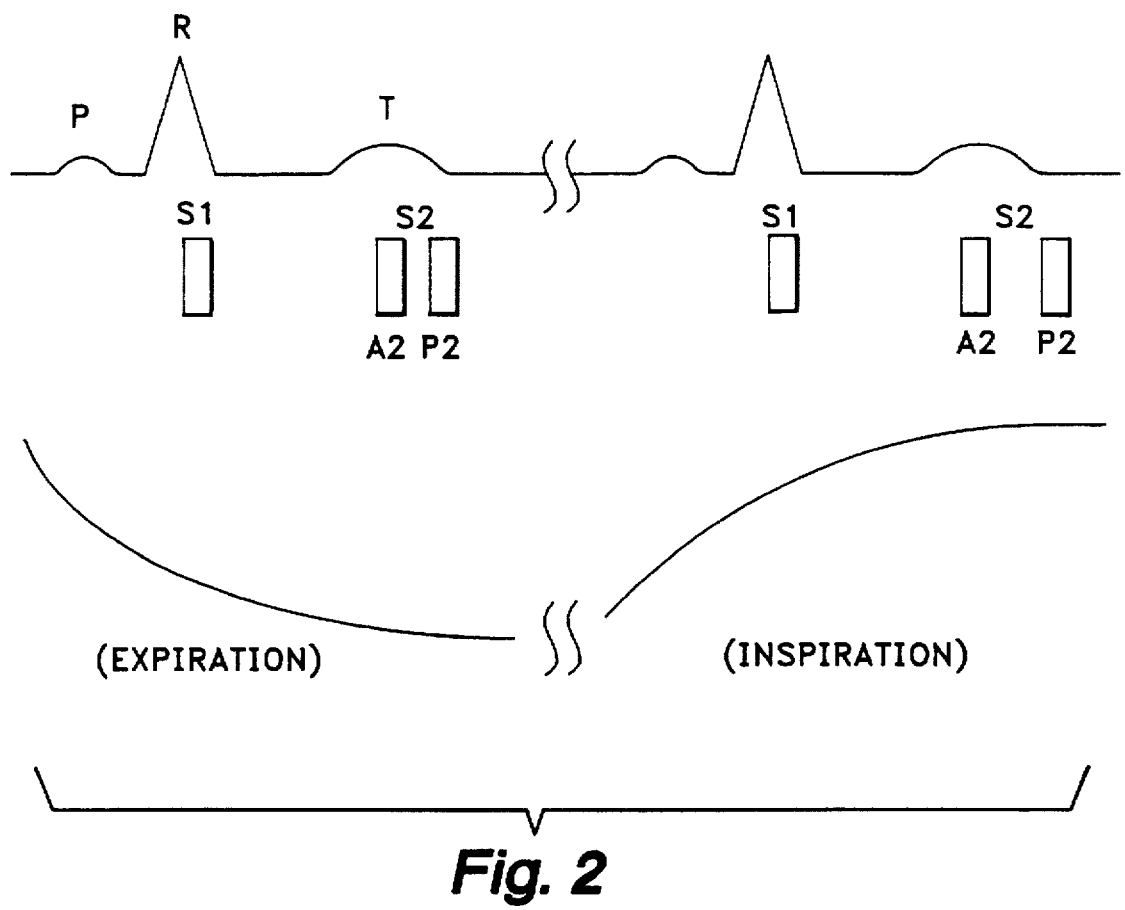
FIG. 2 shows the relationship between the electrical impulse controlling the heartbeat, the respiratory cycle, and normal heart sounds.
Figure 8:
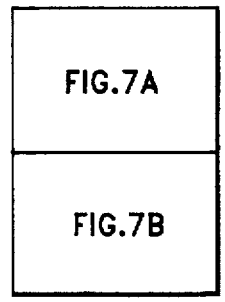
FIG. 8 shows how FIGS. 7A and 7B go together.
Figure 3:
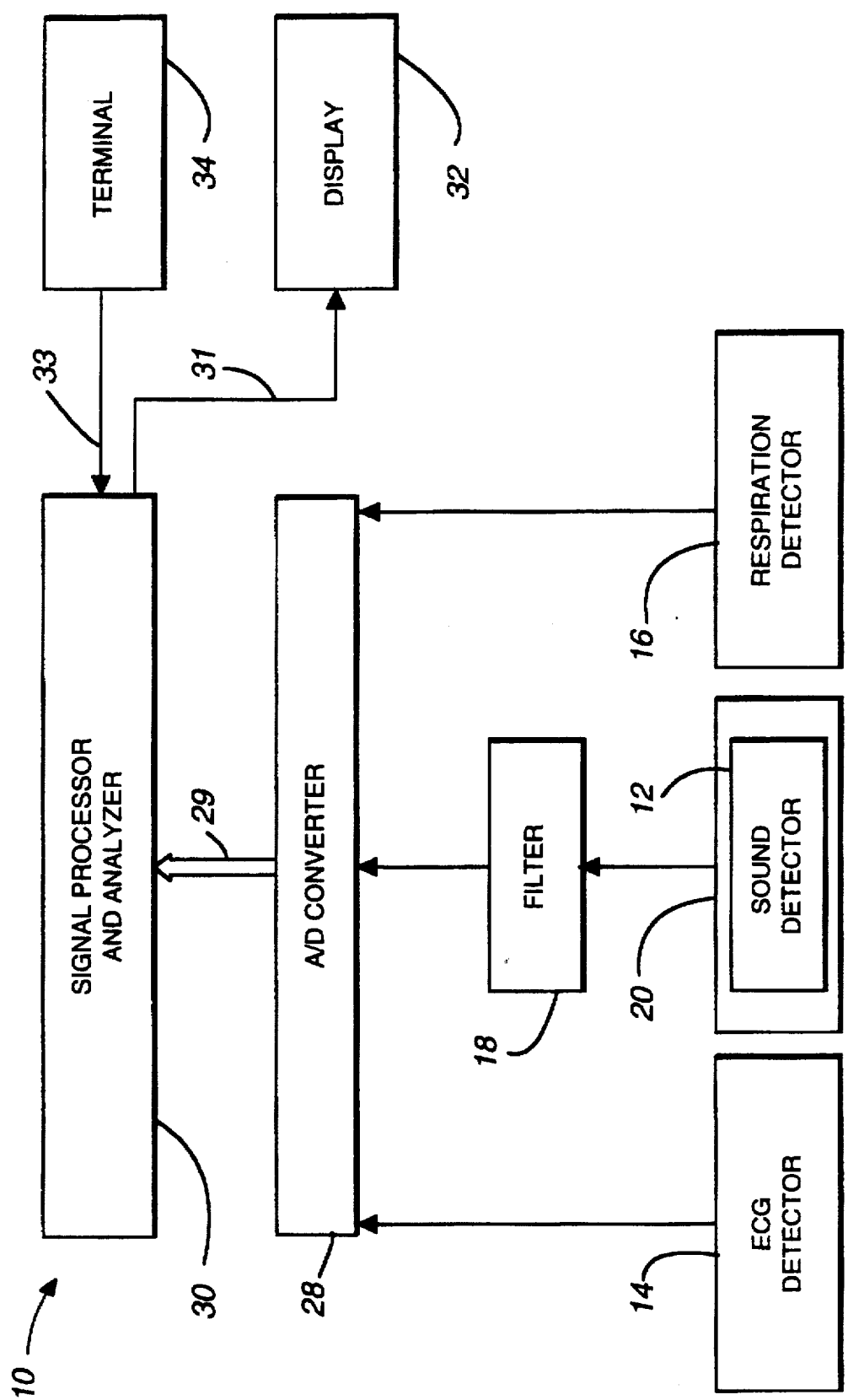
FIG. 3 is a functional block diagram showing the main components of a heart sound analyzer in accordance with the present invention.

FIG. 3 is a functional block diagram showing the main components of a heart sound analyzer 10 in accordance with the present invention. In the preferred embodiment, heart sounds, ECG, and respiration are detected simultaneously and analyzed as a group. Sound detector 12 is a conventional microphone assisted stethoscope having sound shielding 20. Conventional filtering is accomplished by filter 18, and the output signal is provided to analog to digital converter (A/D converter) 28. ECG detector 14 is conventional. ECG detector 14 provides electrical heart signals to A/D converter 28.

Respiration detector 16 is conventional and provides respiration data to A/D converter 28.

A/D converter 28 converts the analog heart sounds, ECG and respiration signals into digital signals 29 for processing by signal processor and analyzer 30. Signal processor and analyzer 30 could be a computer or a microprocessor of various types. One convenient configuration is to have processor 30 be part of a laptop computer with display 32 being the monitor of the laptop and terminal 34 being the keyboard and monitor of the laptop as well. The functions performed by signal processor and analyzer 30 are shown in detail in FIGS. 4 and 5. Visual data and text provided by signal processor and analyzer 30 are displayed on display 32. Examples of the displays generated by processor 30 are shown in FIGS. 6A–6E The physician or other care giver using heart sound analyzer 10 can control the signal processor and analyzer via terminal 34.

Figure 4:
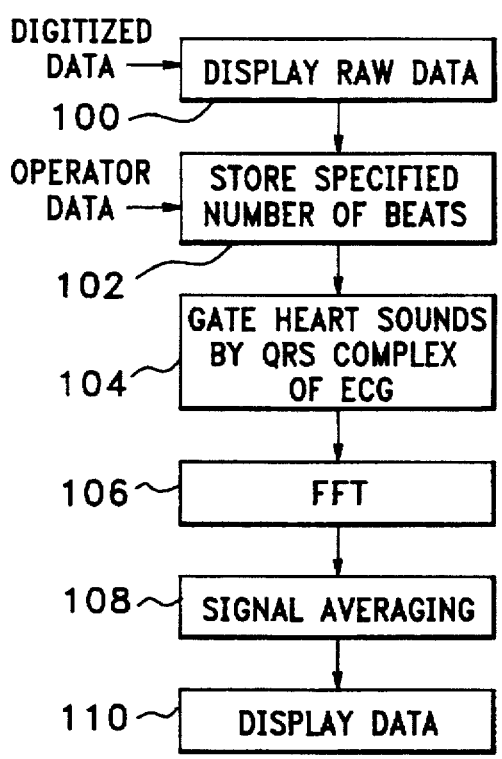
FIG. 4 is a flow diagram showing the process accomplished by the signal processor and analyzer of FIG. 3.

FIG. 4 is a flow diagram showing the basic processes accomplished by signal processor and analyzer 30 of FIG. 3. Processor and analyzer 30 begins in step 100 by displaying the raw heart sounds data received from A/D converter 28 in amplitude versus time format on display 32 via signal 31. When the operator is content with the displayed signal, the operator signals processor 30 via signal 33 from terminal 34 to begin storing data 29. The operator may specify the number of beats to be stored, or this may be a predetermined number stored within processor 30. Processor 30 stores the next specified number of beats by counting the QRS complex signals on the ECG signal in step 102.

Next, in step 104, processor 30 gates the stored heart sounds using the QRS component, so all of the heart sounds are synchronized. In step 106, the fast Fourier transform (FFT) of each stored heart sound is taken. Taking the FFT of each heart sound prevents tiny differences in timing between successive heart sounds from causing data loss in the signal averaging step. Step 108 accomplishes the signal averaging of the FFT signals. Signal averaging improves signal to noise ratio as square root of n, where n is the number of acquisitions (heart sounds stored). Thus, the acquisition does not need to occur in ideal conditions in a sound-proofed room, but can be accomplished in normal doctor's office or hospital settings having a significant amount of background noise.

Finally, in step 110, processor 30 displays the processed data on display 32. FIGS. 6A–6E show how this data will look for various heart conditions.

Figure 5:
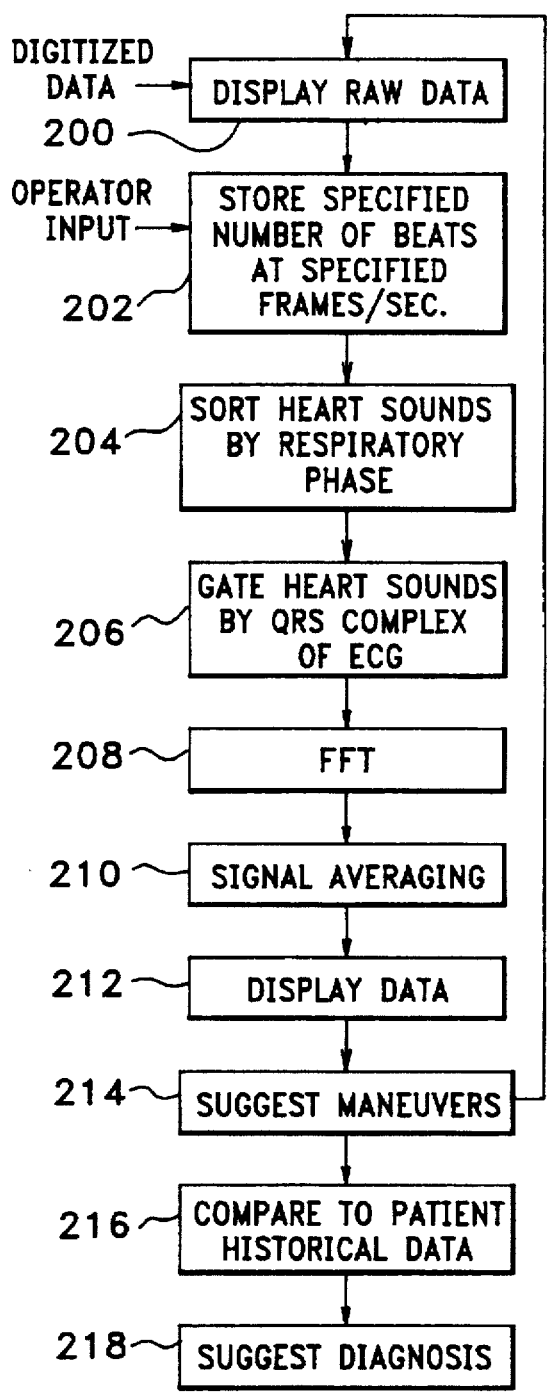
FIG. 5 is a flow diagram showing further functions accomplished by the signal processor and analyzer of FIG. 3.

FIG. 5 shows further functions which may be accomplished by signal processor and analyzer 30 in accordance with the present invention. Processor 30 displays the raw digitized heart sound data from the patient on display 32 in step 200. Operator input 33 from terminal 34 signals processor 30 to begin storing heart sounds in step 202, and may also control the number of beats to store, the number of frames per second to store, and the place of detection and maneuver.

In step 204, processor 30 sorts the heart sounds into two sets, one set acquired during patient inhalation and the other set acquired during patient exhalation. Each stored heart sound is gated by the QRS signal in step 206. The FFT of each stored heart sound is taken in step 208. Signal averaging is accomplished separately on the two sets of heart sounds in step 210. The two signal averaged data sets are displayed in step 221.

Signal processor and analyzer 30 may suggest that the operator perform other maneuvers to collect more data in step 214. If this occurs, process returns to step 200 to collect and process a second set of heart sound data. In any case, once all of the data is collected it is compared to historical patient data in step 216. In step 218, processor 30 suggests a diagnosis. FIG. 7 shows an example of how processor 30 can accomplish the steps of suggesting maneuvers and diagnoses.

Figure 6A:
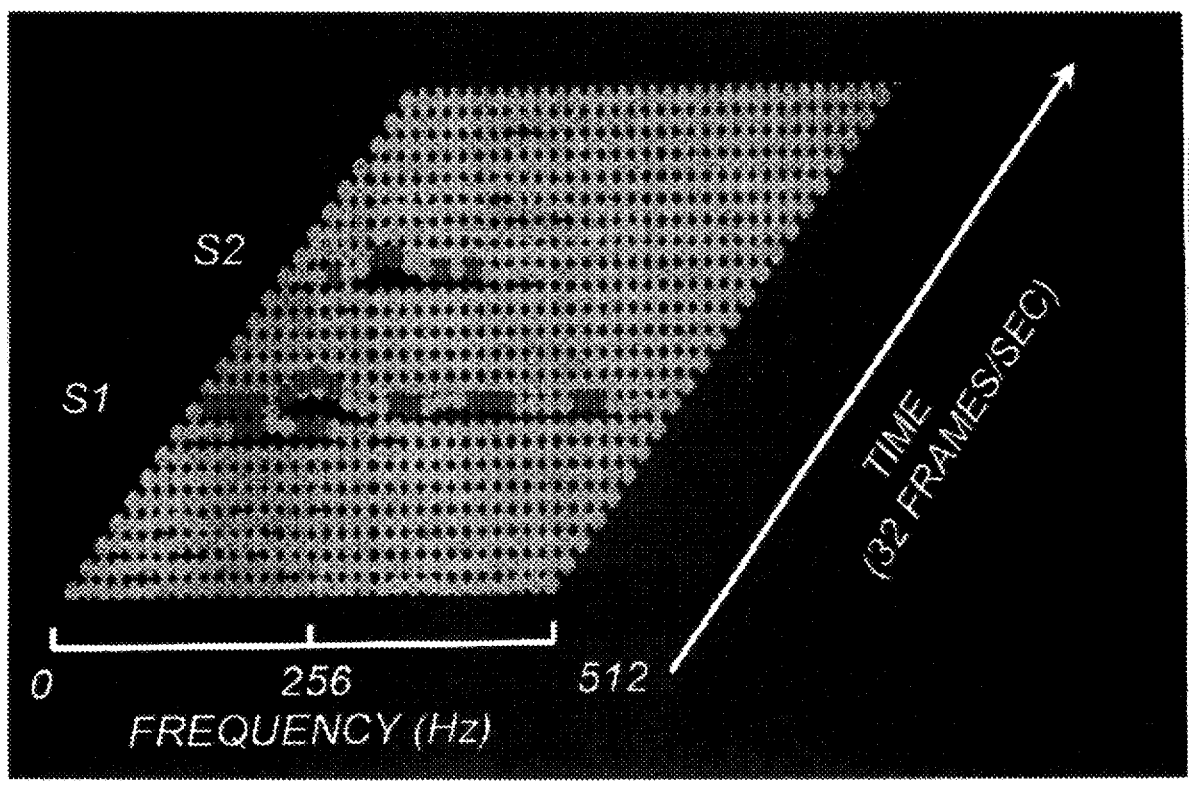
FIG. 6 is composed of FIGS. 6A, 6B, 6C, 6D and 6E and shows displays produced by the signal processor and analyzer of FIG. 3.

FIG. 6 is composed of FIGS. 6A through 6E. FIG. 6A shows how the display of the heart sounds of a patient with a normal heart would look. S1 and S2 are nicely separated, with no extra sounds or murmurs appearing. The x axis shows the frequency of the sounds, with the y axis indicating the time each sound occurred. The color of the dots indicates the intensity of the sound at that time and frequency, with red dots indicating the highest intensity, followed by green dots, then blue, then white. Intensity is also indicated by the height of the dots. Thus, the red dots, indicating highest intensity sound, are furthest elevated above their associated time line.

Figure 6B:
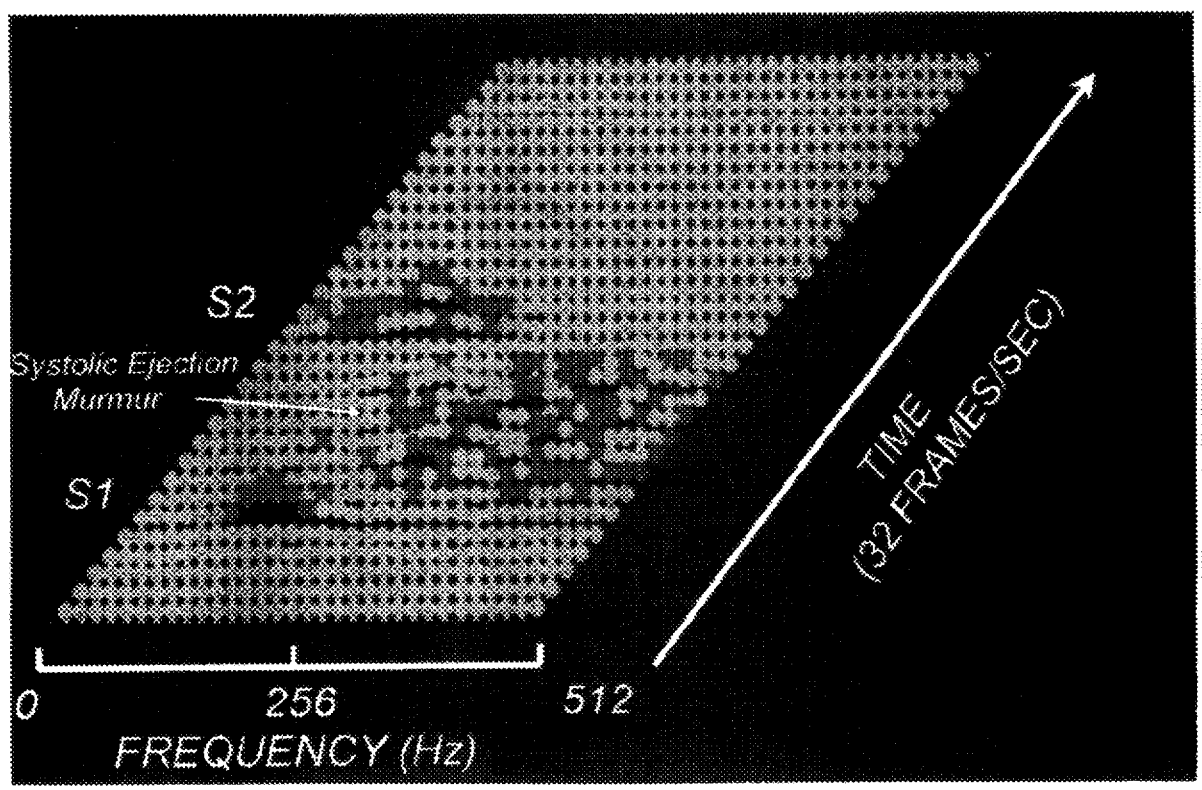

FIG. 6B shows a representative tracing of the heart sounds of a patient with aortic stenosis. Aortic stenosis is generally associated with a soft A2 sound, with a high pitched extra sound (systolic ejection click) in early systole and an associated murmur, and opening snap. See FIG. 7. FIG. 6B demonstrates how the murmur begins after S1 and ends before S2. Moreover, it is clear that the intensity and the frequency of the murmur are not constant.

Figure 6C:
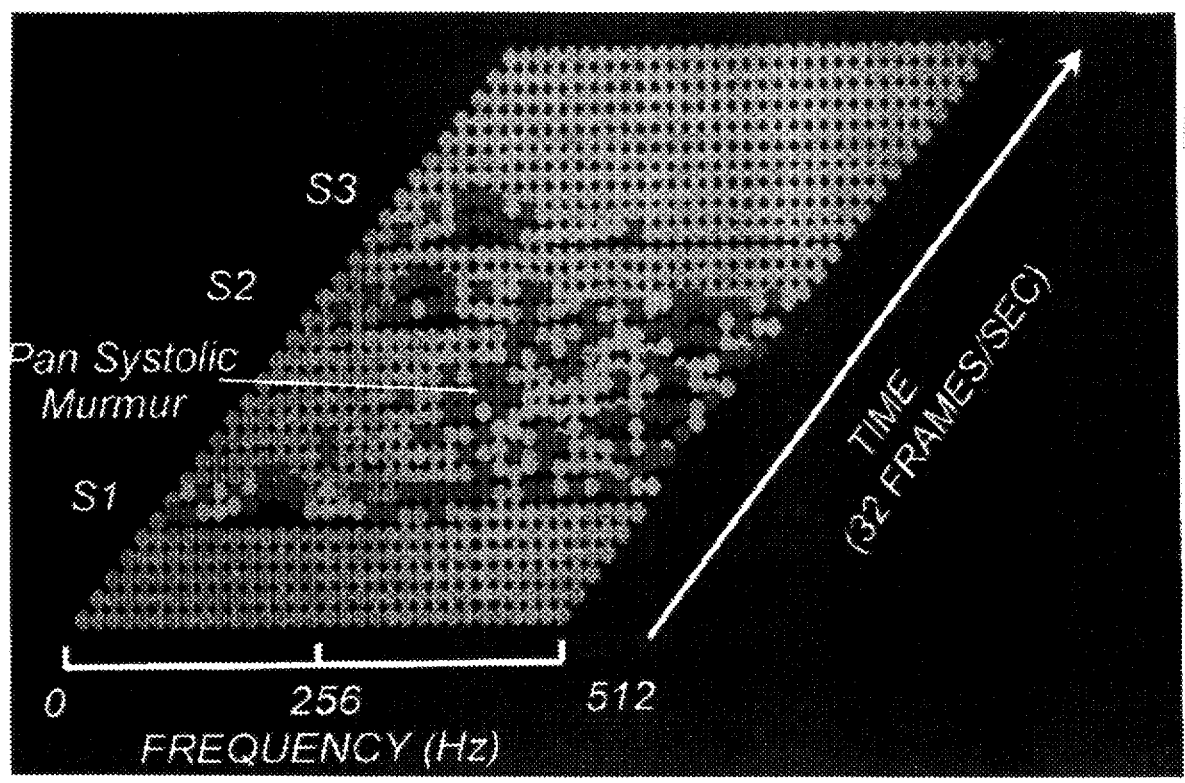

FIG. 6C shows a representative tracing of the heart sounds of a patient with mitral regurgitation. Mitral regurgitation is generally associated with a soft S1 sound and an associated pan-systolic murmur, and is confirmed by hand grip making the murmur louder. FIG. 6C illustrates the presence of the murmur throughout systole.

Figure 6D:
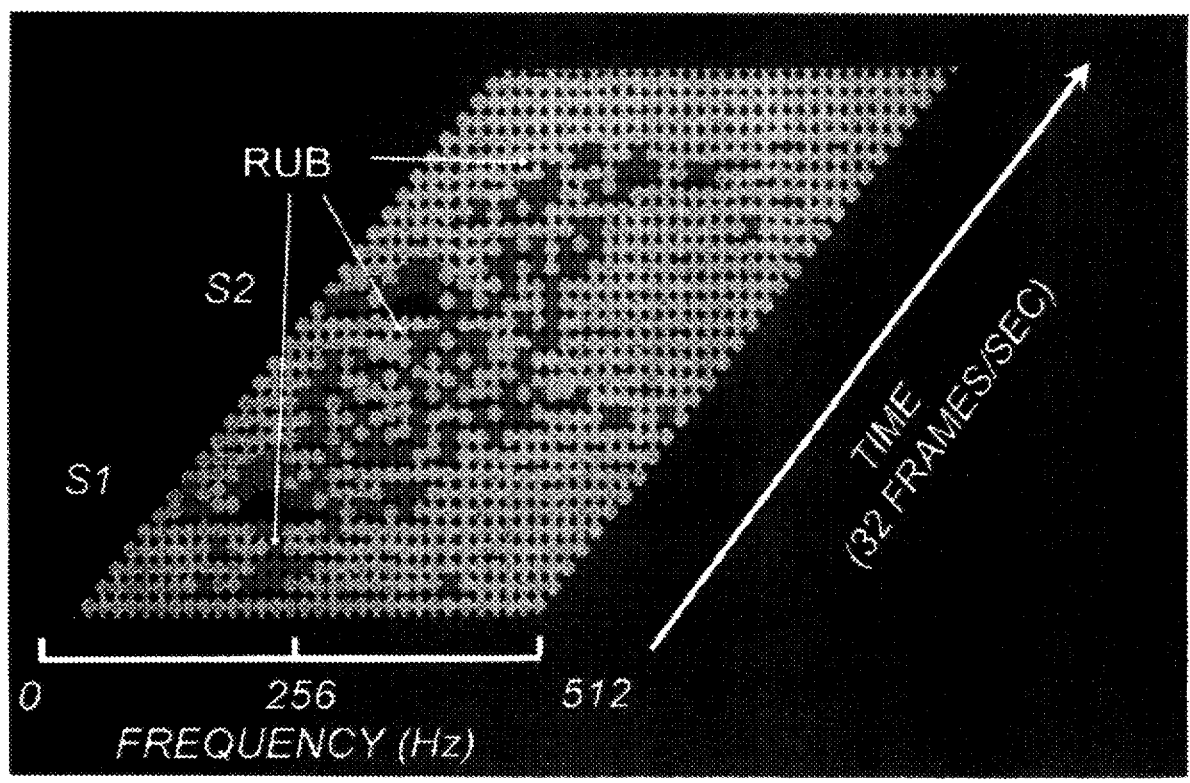

FIG. 6D shows a representative tracing of the heart sounds of a patient having pericardial friction rub. This sound results from rubbing of an inflamed pericardium during the cardiac cycle. Although this may sound like systolic and diastolic murmurs, FIG. 6D confirms a frequency signature to this sound.

Figure 6E:
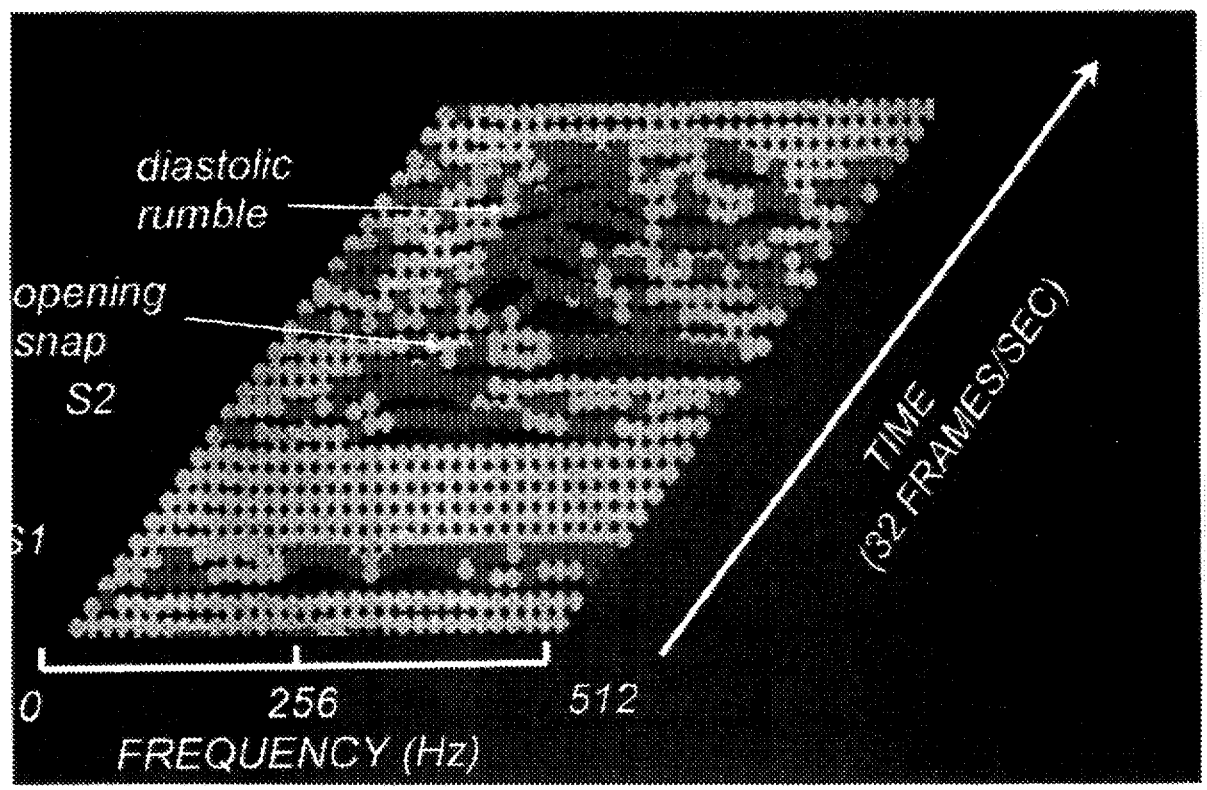

FIG. 6E shows a representative display of the heart sounds of a patient with mitral stenosis. Mitral stenosis is generally associated with a loud M1 sound, a low pitched associated murmur in early diastole and opening snap (see FIG. 7). FIG. 6E shows all of these features.

FIG. 7 is a chart showing an example of a diagnostic approach which could be taken by the signal processor and analyzer 30 in suggesting maneuvers and diagnoses to the heart sound analyzer 10 user. First, abnormal sounds are divided into abnormal sounds, murmurs and other extra heart sounds. Next, sounds are classified according to their timing in the heart sound cycle, and whether the timing is consistent or not. Then the frequency or pitch of the sound is added as a factor. Respiratory phase is examined as a factor. Signal processor and analyzer 30 then suggests a lesion based upon these factors. If a different maneuver will help confirm the diagnosis, signal processor and analyzer 30 displays a request for the user to perform this maneuver. Those skilled in the art will appreciate that computer assisted diagnosis could be based upon these characteristics.

In addition to the obvious application for screening for and diagnosis of anatomic and functional heart disease, another extremely useful capability of the present invention is following the natural history as well as treatment response of a patient once cardiac abnormalities have been documented and characterized. For example, suppose patient's mitral stenosis was detected by the present invention and the mitral valve area was quantified with an additional anatomic test (e.g. echocardiography, costing around $1000 per study). The progression of the stenosis could be followed by the present invention using the timing between the opening snap (OS) and aortic closure (A2) as well as the pitch and intensity of the diastolic murmur. Once the present invention determined that the severity of the lesion had increased to a point which warranted surgical intervention, a follow up echocardiogram could be performed to confirm this conclusion. The documentation and direct quantification of measurements made with the present invention obviates the need for frequently repeated anatomic studies, saving the patient time and money.

While the exemplary preferred embodiments of the present invention are described herein with particularity, those having normal skill in the art will recognize various changes, modifications, additions and applications other than those specifically mentioned herein without departing from the spirit of this invention. For example, some physicians may possess greater skill at interpreting the graphical displays generated by the present invention. Given the digital nature of the data, it would be possible to transfer the data over telephone lines to obtain consultation with expert interpreters.

What is claimed is:

1. Apparatus for analyzing heart sounds utilizing head sound data and respiration data collected from a patient, said apparatus comprising:

means for storing data representing a plurality of heart beat sounds;

means for sorting said data representing a plurality of heart beat sounds according to respiratory phase;

means for taking a fast Fourier transform of the data associated with each stored heart beat sound;

means for signal averaging the fast Fourier transform; and means for providing the averaged fast Fourier transforms to a user, in a format useful for evaluating the patient's heart function.

2. The apparatus of claim 1, further including means for displaying the signal averaged fast Fourier transforms.

3. The apparatus of claim 1 which also utilizes ECG data collected from the patient, said ECG data including QRS complex data, and further including:

means for gating said data representing a plurality of heart beats sounds according to the QRS complex of said ECG data.

4. The apparatus of claim 1 further including:

means permitting an operator to specify when said means for storing stores data.

5. The apparatus of claim 1, further including:

means for providing a signal to an operator of said apparatus, said signal for indicating suggested maneuvers to be performed on said patient.

6. The apparatus of claim 1, further including:

means for comparing the signal averaged fast Fourier transforms to a historical database for said patient.

7. The apparatus of claim 1, further including:

means for selecting a suggested patient diagnosis based upon the signal averaged fast Fourier transforms; and means for providing a signal to an operator of said apparatus, said signal indicating the suggested patient diagnosis.

8. Apparatus for analyzing heart sounds utilizing heart sound data, ECG data including QRS components, and respiration data collected from a patient, said apparatus comprising:

means for storing data representing a plurality of heart beat sounds;

means for sorting said stored data representing a plurality of heart beat sounds according to respiratory phase into a first group stored during patient inspiration and a second group stored during expiration;

means for gating said stored data representing a plurality of heart beat sounds by QRS components of said ECG data;

means for taking a fast Fourier transform of the data associated with each stored heart beat sound;

means for signal averaging the fast Fourier transforms associated with the first group;

means for signal averaging the fast Fourier transforms associated with the second group; and means for providing the signal averaged fast Fourier transforms associated with the first group and the second group to a user, in a format useful for evaluating the patient's heart function.

9. The apparatus of claim 8, further including:

means for displaying said signal averaged fast Fourier transform groups.

10. The apparatus of claim 9, further including:

means for providing a first signal to an operator of said apparatus, said first signal indicating suggested maneuvers to be performed on said patient.

11. The apparatus of claim 10, further including:

means for comparing the signal averaged fast Fourier transforms to a historical database for said patient.

12. The apparatus of claim 11, further including:

means for selecting a suggested patient diagnosis based upon the signal averaged fast Fourier transforms; and means for providing a second signal to the operator, said second signal indicating the suggested patient diagnosis.

13. A method for analyzing heart sounds utilizing heart sound data and respiration data collected from a patient, said method comprising the steps of:

storing data representing a plurality of heart beat sounds;

sorting said data representing a plurality of heart beat sounds according to respiratory phase;

taking a fast Fourier transform of the data associated with each stored heart beat sound;

signal averaging the fast Fourier transforms; and providing the averaged fast Fourier transforms to a user, in a format useful for evaluating the patient's heart function.

14. The method of claim 13, further including the step of displaying the signal averaged fast Fourier transforms.

15. The method of claim 13 which also utilizes ECG data collected from the patient, and further including the step of:

gating said data representing a plurality of heart beat sounds by QRS complex of said ECG data.

16. The method of claim 13 further including the step of:

permitting an operator to specify when said storing step stores data.

17. The method of claim 13, further including the step of:

providing a signal to an operator, said signal for indicating suggested maneuvers to be performed on said patient.

18. The method of claim 13, further including the step of:

comparing the signal averaged fast Fourier transforms to a historical database for said patient.

19. The method of claim 13, further including the steps of:

selecting a suggested patient diagnosis based upon the signal averaged fast Fourier transforms; and providing a signal to an operator, said signal indicating the suggested patient diagnosis.

* * * * *